US007047057B2

(12) United States Patent
Hall et al.

(10) Patent No.: US 7,047,057 B2
(45) Date of Patent: May 16, 2006

(54) SIMULTANEOUS MULTIWAVELENGTH TPSF-BASED OPTICAL IMAGING

(75) Inventors: David Hall, Montréal (CA); Richard Boudreault, Ville St-Laurent (CA); Pierre A. Beaudry, Pierrefonds (CA)

(73) Assignee: ART. Advanced Research Technologies Inc., Montréal (CA)

( * ) Notice: Subject to any disclaimer, the term of this patent is extended or adjusted under 35 U.S.C. 154(b) by 10 days.

(21) Appl. No.: 10/050,941

(22) Filed: Jan. 22, 2002

(65) Prior Publication Data

US 2003/0085338 A1 May 8, 2003

Related U.S. Application Data

(60) Provisional application No. 60/305,080, filed on Jul. 16, 2001.

(51) Int. Cl.
*A61B 5/00* (2006.01)
(52) U.S. Cl. .................. 600/407; 600/476; 356/432
(58) Field of Classification Search ................ 600/473, 600/407, 476–478, 425; 250/363.02; 356/300, 356/320, 337, 432
See application file for complete search history.

(56) References Cited

U.S. PATENT DOCUMENTS

| 5,694,938 | A | * | 12/1997 | Feng et al. ............... 600/425 |
| 5,987,351 | A | * | 11/1999 | Chance ...................... 600/473 |
| 6,339,216 | B1 | * | 1/2002 | Wake ...................... 250/214 A |
| 6,509,729 | B1 | * | 1/2003 | Levitt ...................... 324/76.36 |
| 2001/0027316 | A1 | * | 10/2001 | Gregory ................... 606/15 |

* cited by examiner

*Primary Examiner*—Ruth S. Smith
(74) *Attorney, Agent, or Firm*—Bereskin & Parr; Luc Bérubé

(57) ABSTRACT

The TPSF-based imaging technique uses multiple wavelengths to image an object simultaneously. Acquisition time of an image can be shortened without sacrificing the effective amount or quality of raw imaging data acquired. A plurality of distinguishable wavelengths may be used simultaneously at different injection-detection positions to acquire simultaneously a plurality of TPSF-based imaging data points for the different injection-detection positions. The multiple wavelengths may provide complementary information about the object being imaged.

15 Claims, 3 Drawing Sheets

SIMULTANEOUS MULTIWAVELENGTH TPSF-BASED OPTICAL IMAGING

CROSS-REFERENCE TO RELATED APPLICATIONS

The application claims priority of U.S. provisional application Ser. No. 60/305,080 filed on Jul. 16, 2001 entitled "Simultaneous multiwavelength TPSF-based optical imaging".

FIELD OF THE INVENTION

The present invention relates to the field of temporal point spread function (TPSF) based imaging in which objects which diffuse light, such as human body tissue, are imaged using signals resulting from the injection of light into the object and detection of the diffusion of the light in the object at a number of positions while gathering TPSF-based data to obtain information beyond simple attenuation such as scattering and absorption. More particularly, the present invention relates to a method and apparatus for simultaneous multi-wavelength TPSF-based imaging which reduces image acquisition time, and also promises to provide enhanced image information.

BACKGROUND OF THE INVENTION

Time-domain optical medical images show great promise as a technique for imaging breast tissue, as well as the brain and other body parts. The objective is to analyze at least a part of the temporal point spread function (TPSF) of an injected light pulse as it is diffused in the tissue, and the information extracted from the TPSF is used in constructing a medically useful image.

Two fundamental techniques are known by which the TPSF can be obtained: time domain and frequency domain. In time domain, a high intensity, short duration pulse is injected and the diffused light is detected within a much longer time frame than the pulse, but nonetheless requiring high-speed detection equipment. In frequency domain, light is modulated in amplitude at a range of frequencies from the kHz range to about 0.5 GHz. The light injected is modulated but essentially continuous, and the information collected is the amplitude and the phase difference of the light at the detector. Thus, lower intensities are required, and the demands of very short, high intensity injection pulse generation and high-speed detection are avoided. The acquisition of the data requires the two parameters of amplitude and phase shift to be recorded for a large number of modulation frequencies within the dynamic range provided. The TPSF could be calculated by inverse Fourier transform, however, the image is typically generated using the frequency domain data.

In optical imaging of human breast tissue, the breast is immobilized by stabilizing plates of the optical head. Although the light injected is not harmful, prolonged imaging time is uncomfortable for patients, particularly in the case of female breast imaging in which the breast is typically secured between support members or plates, and is typically immersed in a bath or surrounded by a coupling medium contained in a bag. While optical imaging promises a safer and potentially a more medically useful technique, imaging time and related patient discomfort remains a problem in providing a competitively superior technique.

To maintain the objective of acquiring the best quality images that the technology will permit, a minimum acquisition time is required. This acquisition time required to generate quality medical images determines the cost efficiency of the imaging equipment. Thus a reduction in imaging time will result in greater throughput.

SUMMARY OF THE INVENTION

It is an object of the present invention to provide a method and apparatus for TPSF-based imaging of an object in which acquisition time of an image can be shortened without sacrificing the effective amount or quality of raw imaging data acquired.

According to one broad aspect of the invention, this object is achieved by using a plurality of distinguishable wavelengths simultaneously to acquire simultaneously a plurality of TPSF-based imaging data points. Advantageously, different injection-detection positions may be used simultaneously to collect imaging data points simultaneously for the different injection-detection positions, thus covering more imaging area faster. Also preferably, the wavelengths may provide complementary information about the object being imaged.

According to the invention, there is provided a method of TPSF-based optical imaging comprising the steps of injecting light at a plurality of wavelengths into an object to be imaged at one or more injection positions, and detecting the injected light after diffusing in the object at one or more detection positions simultaneously for the plurality of wavelengths to obtain separate TPSF-based data for each of the wavelengths.

The invention also provides a TPSF-based optical imaging apparatus comprising at least one source providing light at a plurality of wavelengths, a plurality of injection ports and lightguides coupled to the at least one source for injecting the light into an object to be imaged at one or more injection positions, a plurality of detection ports and lightguides, a wavelength selection device coupled to the plurality of detection ports and lightguides for separating the plurality of wavelengths, and a camera detecting the plurality of wavelengths separated by the device.

BRIEF DESCRIPTION OF THE DRAWINGS

The invention will be better understood by way of the following detailed description of a preferred embodiment and other embodiments with reference to the appended drawings, in which.

DETAILED DESCRIPTION OF THE PREFERRED EMBODIMENT

In the preferred embodiment, the invention is applied to the case of time domain optical medical imaging, however, it will be apparent to those skilled in the art that the invention is applicable to frequency domain techniques for optical imaging. The injected pulses at each of the plurality of wavelengths are preferably simultaneously injected, however, for the imaging to be "simultaneous", the time window reserved for acquiring the TPSF from a single wavelength's injection pulse using the chosen detector overlaps between the respective wavelengths even if the injected pulses were not simultaneous. In the preferred embodiment, it is important to respect the temporal resolution of the detector as better described hereinbelow.

Figure 1:
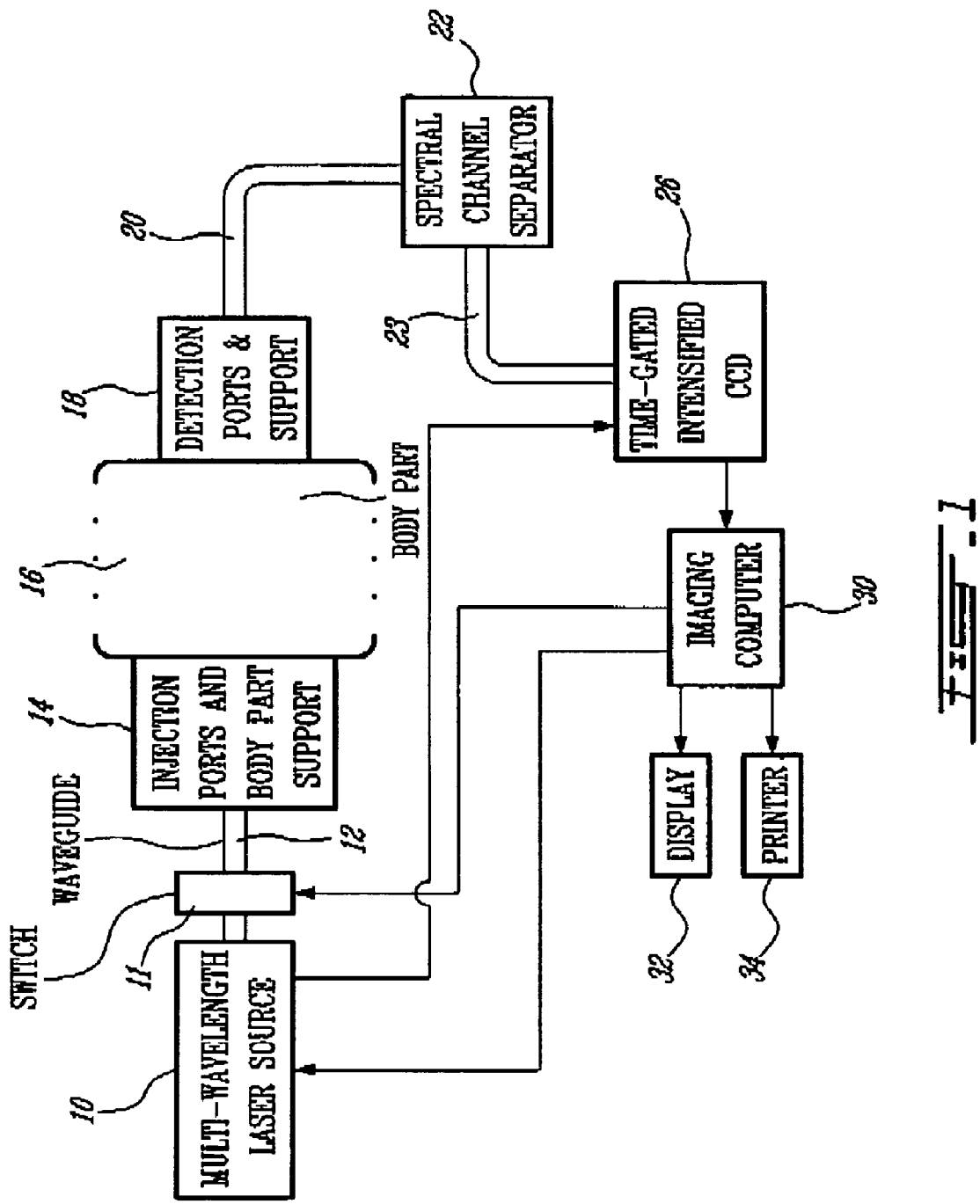
FIG. 1 illustrates schematically the components of the imaging system according to the preferred embodiment including the laser sources, injection and detection port apparatus, multiwavelength detector, detector signal processor and imaging computer station.

As illustrated in FIG. 1, the pulsed light source 10 has an output (in practice, it will comprise a plurality of laser source outputs at discrete wavelengths, as described further hereinbelow) optically coupled via a switch 11 to one of plurality of waveguides 12 to a number of injection ports of a support 14. The injection ports are preferably positioned at a number of fixed positions over the imaging area for each wavelength to be used, although the injection port may alternatively be movable over the body surface, provided that the body part 16 is immobilized. As is known in the art, the injection and detection ports may directly contact the body or a coupling medium may be used between the body and the injection/detection ports. The detection ports and support 18 are arranged in FIG. 1 in transmission mode for breast imaging. It also possible to arrange detection ports on the same surface of the patient as the injection ports, in which case imaging is achieved by measuring the TPSF of the diffused pulse reflected from the tissue.

The light injected is preferably pulses having a duration of about 1 to 100 picoseconds and an average power of about 100 mW. The laser source 10 preferably comprises four laser sources operating at 760 nm, 780 nm, 830 nm, and 850 nm. These different wavelengths allow for complementary information to be acquired to build a physiological image of the breast tissue. As better shown in FIG. 2, the output of each wavelength laser source 10a to 10d, for the four wavelengths chosen, are coupled to fibers 12a to 12d respectively. The fibers are preferably multimode fibers, such as 200/240 micron graded index multimode fibers.

Figure 2:
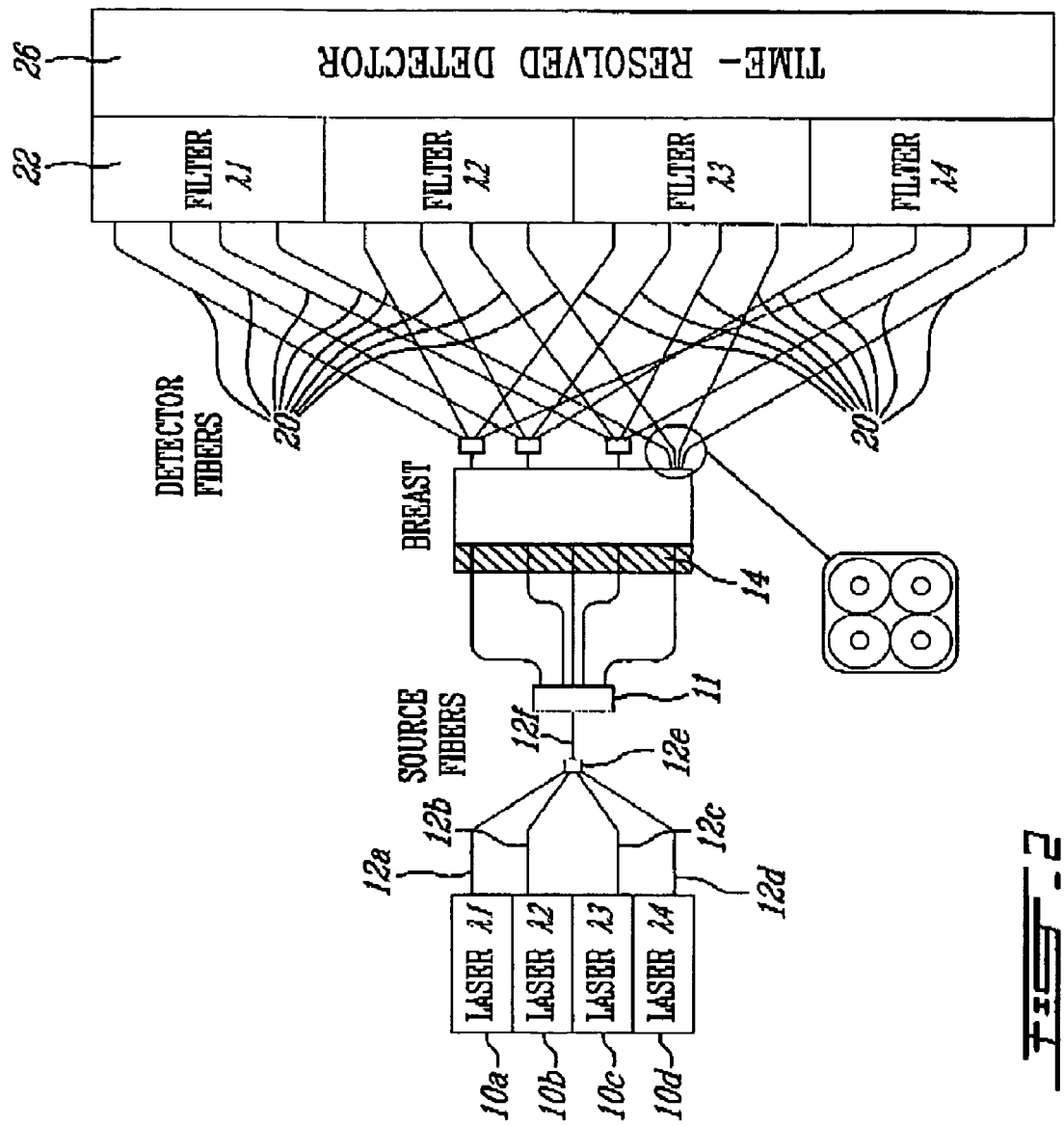
FIG. 2 illustrates an optical schematic diagram of the imaging system according to the preferred embodiment showing the multiple waveguide paths between the detection ports and the detector, as well as the multiplexed multiple wavelength source arrangement.

Although FIG. 2 illustrates for simplicity four injection positions and four detection positions, it will be understood that there may be about 10 injection positions and typically up to about 50 detector positions. The light from the four sources is preferably injected at the same point, and the light is coupled onto a same fiber 12f, as shown in FIG. 2, using a coupler 12e, or alternatively the four fibers 12a to 12d could be fed as a bundle to the same position within support 14. It will be appreciated that multiplexing the four wavelengths onto the same fiber 12f allows a conventional single wavelength support 14 to be used without taking into account different injection positions within the program of the imaging computer or processor 30. It is of course possible to have injection positions unique to each wavelength, however, to reduce the number of support positions while maintaining the same number of injection source locations at any chosen wavelength, it is preferred to provide multiplexed signals on single fibers or bundled fibers at each injection/detection site.

While FIG. 2 illustrates a single fiber (or bundle) 12f, there is preferably 10 such fibers for the 10 injection positions. A fiber switch 11, such as a conventional 1 by 32 JDS Uniphase switch is used to switch light from each laser source 10 to a desired one of the injection port positions.

Figures 3, 4:
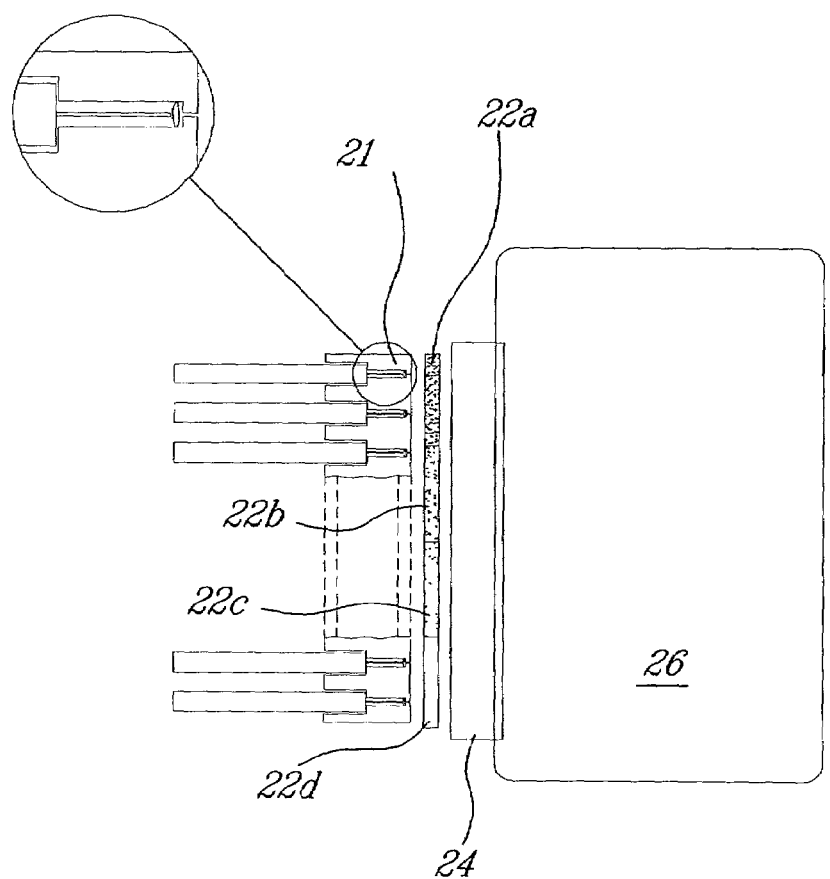
FIG. 3 illustrates a side view of the detection fibers coupled to a detector using a collimating fiber holder.
FIG. 4 illustrates a plan view of the detector faceplate surface having four quadrants each provided with a different wavelength selective filter coating.

The detected optical signals are communicated by waveguides 20, namely 400/440 micron graded index multimode optical fibers, to a spectral channel separator 22, namely a series of filters in the preferred embodiment. As also shown in FIGS. 3 and 4, the filters may comprise band-pass filter coatings 22a, 22b, 22c, and 22d on a faceplate 24 of the detector 26. Each detection fiber 20 is coupled directly to the detector 26 without switching, in the preferred embodiment. While it is possible for the separator 22 to switch and/or demultiplex the light from fibers 20 onto lightguides 23, as illustrated in FIG. 1, in the preferred embodiment shown in FIGS. 3 and 4, the fibers 20 are mounted in a collimating fiber holder or positioner 21 for directing the light from each fiber 20 to the filter 22 and then onto the detector surface 26. The collimating holder has a collimating microlens for coupling the light exiting the core of the fiber 20 onto the detector surface with a small spot size. In the preferred embodiment, there are 50 detector ports 18, with 200 fibers 20. Thus an array of 50 fibers is arranged in each quadrant or zone of the faceplate 24 at the detector 26. It will be appreciated that spectral separation may also be achieved using an optical spectrometer or a grating device, such as an arrayed waveguide grating or the like, instead of using a filtering medium or coating. Preferably, the injection and detection locations are the same for each wavelength, however, individual positions for lightguides for each wavelengths can be accommodated, e.g. the detector ports could support 200 positions fiber.

The wavelength separated signals are all detected simultaneously by a gated intensified CCD camera, for example a PicoStar Camera by LaVision. The camera 26 is used to detect the light from each detection port 18 and at each desired wavelength with picosecond resolution. The injected pulse may spread out over several picoseconds to several nanoseconds as a result of diffusion through the body tissue.

A large number of pulses are injected and their corresponding camera signals are processed by imaging computer 30 to determine one data point, i.e. the temporal point spread function for a particular wavelength and a particular injection port and detection port combination. For a given injection position, the TPSF is measured at a number of detector positions at which the detected signal provides good signal to noise. Such data points are gathered for a large number of combinations of wavelengths and port positions to obtain sufficient "raw" data to begin constructing an image of the tissue. The resulting image can be displayed on display 32 and printed on a printer 34.

It will also be appreciated that using different detector positions simultaneously for a single injector position allows for off-axis information to be used. The image processing is thus adapted to take into consideration the geometry related to the off-axis data, however, the combination of on-axis and off-axis data is more accurate and provides faster acquisition with better resolution and/or image robustness.

The imaging computer 30 is also responsible for signaling a laser source 10 to select a desired wavelength and then switch that wavelength signal to a desired output fiber 12. The computer 30 thus progresses through all desired wavelength and position combinations to achieve the desired imaging. The laser source 10 synchronizes the camera 26 with each pulse. The laser source 10 may also comprise a number of fixed wavelength optical sources, as it may also comprise a single broadband source.

It will be appreciated that in the case of frequency domain optical imaging, the laser 10 will be controlled to be modulated at the desired frequency and switch its output onto the desired fiber 12. In this case, the computer 30 will then need to sweep through a large number of modulation frequencies at which the amplitude and phase shift of the detected light is recorded with good accuracy. The TPSF for a single data point can be calculated from the amplitude and phase shift data set recorded, or typically, the frequency domain data is used directly to reconstruct the image.

In the present application, reference is made to a plurality of wavelengths that can be separately detected. While these distinct wavelengths can be generated from a monochromatic or broadband light source to directly provide the desired wavelengths, it is alternatively possible to mix a first basic wavelength with a second reference wavelength to create a beating of the wavelengths. This can be used to tune the basic wavelength to create the desired wavelength at the plurality of wavelengths and is another way of providing the light to be injected according to the invention. Given that the light source has two parts for the first and second wavelengths, it is possible to control or pulse only one to achieve the desired light injection.

What is claimed is:

1. A method of Temporal Point Spread Function (TPSF)-based optical imaging comprising the steps of:
   injecting light at a plurality of wavelengths into an object to be imaged at one or more injection positions;
   collecting the injected light after diffusing in the object at one or more collection positions;
   spectrally separating said collected light into individual wavelength signals;
   directing individual wavelength signals at distinct locations on a CCD camera;
   simultaneously detecting said individual wavelength signals using said CCD camera to obtain separate TPSF-based data for each of the wavelengths; and
   wherein said separating and said detecting preserves time-based information of each individual wavelength signal.

2. The method as claimed in claim 1, wherein said plurality of wavelengths provide different information about said object.

3. The method as claimed in claim 2, wherein said imaging is medical imaging, and said different information is complementary to provide physiological information.

4. The method as claimed in claim 1, wherein said step of injecting comprises:
   generating light from a laser light source; and
   switching said light from said light source onto one of a plurality of optical fibers each corresponding to one of said injection positions.

5. The method as claimed in claim 4, wherein said light source comprises a plurality of lasers each operating at one of said plurality of wavelengths.

6. The method as claimed in claim 5, wherein an output of said lasers are combined prior to said switching, said injection position being the same at one time for all of said wavelengths.

7. The method as claimed in claim 6, wherein said plurality of wavelengths provide different information about said object.

8. The method as claimed in claim 1, wherein said step of collecting comprises positioning a bundle of optical fibers at each one of said one or more collection positions, each fiber of said bundle being for a separate one of said wavelengths.

9. The method as claimed in claim 8, wherein said step of collecting comprises placing a faceplate bandpass filter over said CCD camera and positioning together groups of optical fibers for a same wavelength over said filter.

10. The method us claimed in claim 1, wherein said imaging is medical imaging.

11. The method as claimed in claim 1, wherein said step of injecting comprises injecting said light at each of said wavelengths simultaneously at different injection positions, wherein said injected light traveling to at least some of said collection positions comprises light of more than one of said wavelengths.

12. The method as claimed in claim 11, wherein said plurality of wavelengths provide a same information about said object, said method allowing faster acquisition of said data over an imaging area.

13. A Temporal Point Spread Function (TPSP)-based optical imaging apparatus comprising:
   at least one source providing light at a plurality of wavelengths;
   at least one injection port coupled to said at least one source for injecting said light into an object to be imaged at one or more injection positions;
   at least one detection port collecting said light after diffusion in said object;
   a wavelength selection device coupled to said at least one detection port for separating said plurality of wavelengths;
   a CCD camera detecting said plurality of wavelengths separated by said device; and
   an optical guiding device for directing said plurality of wavelength at distinct locations on said CCD camera.

14. The apparatus as claimed in claim 13, wherein said at least one source comprises a plurality of tunable lasers.

15. The apparatus as claimed in claim 13, wherein said at least one source is selectively connected to one of a plurality of said injection ports using an optical switch.

* * * * *